United States Patent
Iddan

(10) Patent No.: US 7,684,601 B2
(45) Date of Patent: Mar. 23, 2010

(54) METHOD AND APPARATUS FOR IMAGING TISSUES

(75) Inventor: Gavriel J. Iddan, Haifa (IL)

(73) Assignee: Microsoft International Holdings B.V., Amsterdam (NL)

( * ) Notice: Subject to any disclaimer, the term of this patent is extended or adjusted under 35 U.S.C. 154(b) by 386 days.

(21) Appl. No.: 11/838,115

(22) Filed: Aug. 13, 2007

(65) Prior Publication Data
US 2007/0276256 A1 Nov. 29, 2007

Related U.S. Application Data

(63) Continuation of application No. PCT/IL2006/000196, filed on Feb. 15, 2006.

(51) Int. Cl.
*G06K 9/00* (2006.01)
(52) U.S. Cl. ........................ 382/128; 382/131; 382/132; 128/922
(58) Field of Classification Search ................ 382/128, 382/130, 131, 132; 128/920, 922
See application file for complete search history.

(56) References Cited

U.S. PATENT DOCUMENTS

| 4,649,275 | A | | 3/1987 | Nelson et al. | |
|---|---|---|---|---|---|
| 5,803,082 | A | | 9/1998 | Stapleton et al. | |
| 5,818,900 | A | * | 10/1998 | Vogelsong et al. | ............ 378/62 |
| 6,057,909 | A | | 5/2000 | Yahav et al. | |
| 6,091,905 | A | | 7/2000 | Yahav et al. | |
| 6,100,517 | A | | 8/2000 | Yahav et al. | |
| 6,331,911 | B1 | | 12/2001 | Manassen et al. | |
| 6,483,094 | B1 | | 11/2002 | Yahav et al. | |
| 6,520,912 | B1 | * | 2/2003 | Brooks et al. | ................ 600/437 |
| 6,740,883 | B1 | * | 5/2004 | Stodilka et al. | ......... 250/363.04 |
| 7,107,116 | B2 | * | 9/2006 | Geng | .......................... 700/117 |
| 7,180,074 | B1 | * | 2/2007 | Crosetto | ................. 250/370.09 |

FOREIGN PATENT DOCUMENTS

WO    WO 2006/030413    3/2006

* cited by examiner

*Primary Examiner*—Yosef Kassa
(74) *Attorney, Agent, or Firm*—Vierra Magen Marcus & DeNiro LLP

(57) ABSTRACT

Method and apparatus for imaging tissue by upstream illumination and downstream dual filtering of the exiting light for separation of ballistic photons rays from stray rays. Dual filtering includes spatial filtering via a pinhole and spatial filtering operated by a fast gate. A processor synchronizes flashes of illumination with the fast gate to command opening for passage of the ballistic photons rays and closure to exclude the stray rays. An image detector downstream of the fast gate collects the ballistic photons rays for processing by the processor and display on a monitor as a shadowgram. Illumination flashes have one or more wavelengths and the image detector is adapted to match the selected wavelengths of the illuminating flashes.

32 Claims, 3 Drawing Sheets

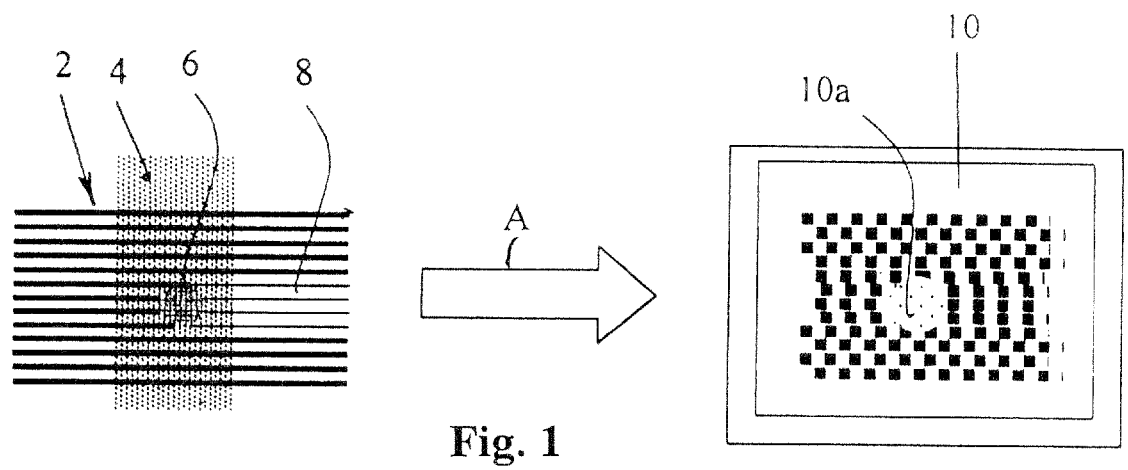
Fig. 1
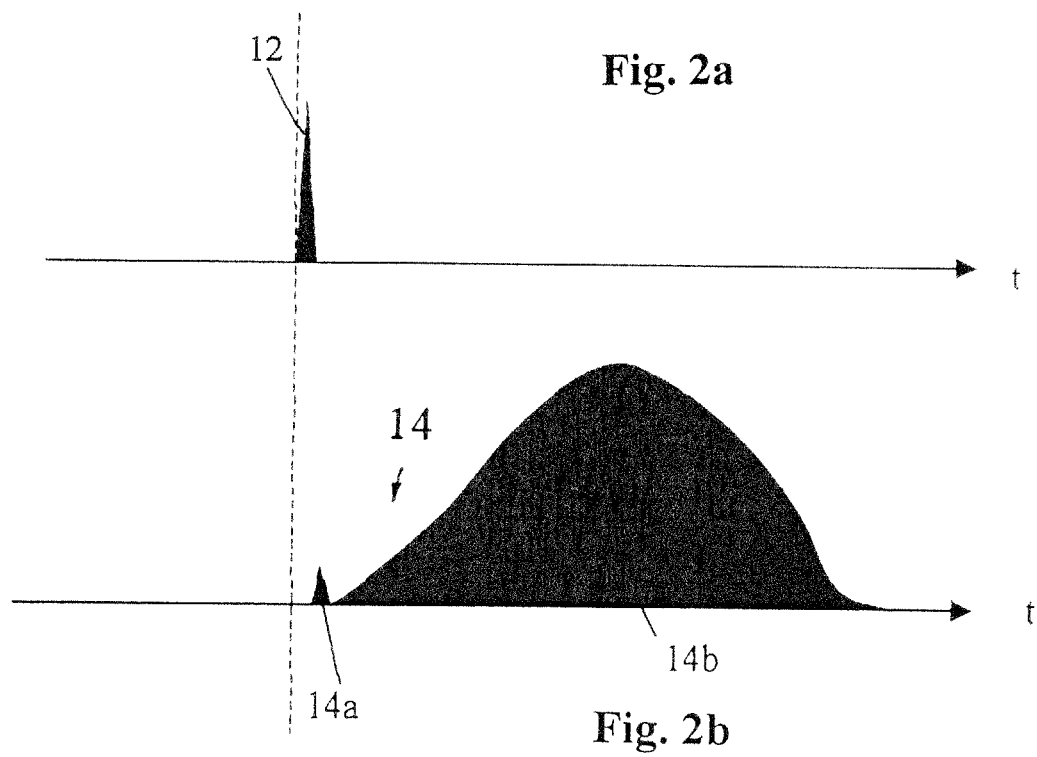
Fig. 2a
Fig. 2b

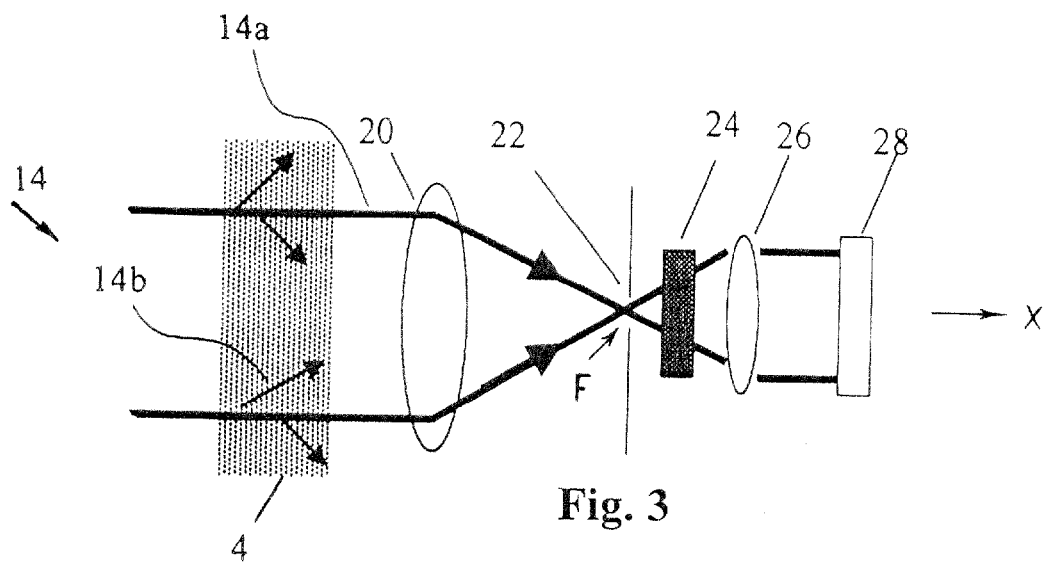
Fig. 3
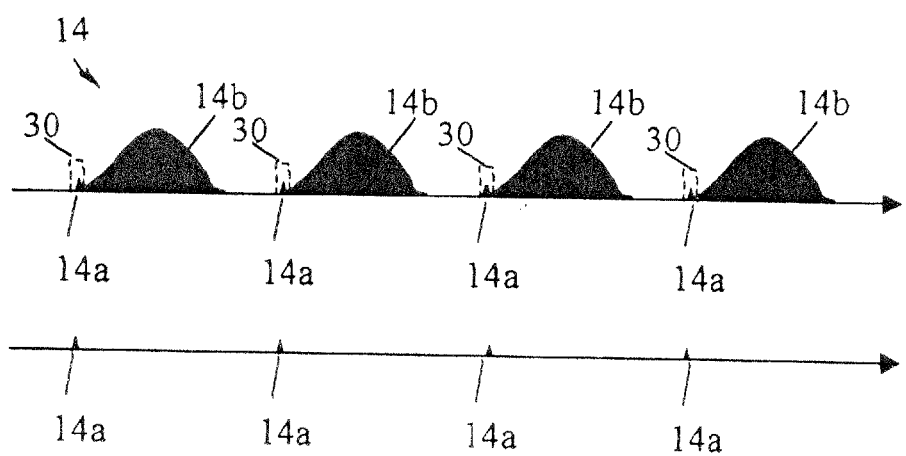
Fig. 4a
Fig. 4b

METHOD AND APPARATUS FOR IMAGING TISSUES

This application is a Continuation of PCT/IL2006/000196 filed Feb. 15, 2006, the priority date of which is claimed herein, and the entire disclosure of which is incorporated herein by reference.

FIELD OF THE INVENTION

The present invention relates in general to a method and apparatus for imaging bodily tissues without using X-rays, and in particular to the use of pulses of light to detect non-uniformity or non-conformity hidden in tissues. Direct rays of photons traversing the examined tissues in the shortest possible trajectory are collected to form a shadowgram image, while stray rays are blocked.

BACKGROUND ART

Imaging of the interior of soft tissues of the body, such as the female breast has been approached in the past by all known modalities, including ultra sound, X-ray, CT, MI and IR illumination, primarily for the purpose of detecting cancer.

A commonly used imaging method for breast cancer detection is mammography, which employs imaging by use of X-rays. Although this last method is accepted as the gold standard for breast cancer detection, it is not an optimal approach since it suffers from several well-known drawbacks. These drawbacks include involving the examinee to an unpleasant and uncomfortable procedure, also involving exposure to X-ray radiations. Furthermore, there is need to operate expensive equipment which is not available in the office of a practitioner but only in clinics, and the practitioner is required to deal with results providing only low resolution images.

Another method of detection relates to ultrasound technology, actually inexpensive, does not require exposure to X-rays but unfortunately, offers only unacceptable limited resolution.

It has been proposed in the past that IR imaging of soft tissues could become a good alternative to X-rays mammography, eliminating almost all the drawbacks listed hereinabove.

According to the U.S. Pat. No. 5,803,082 to Stapleton et al., proposes an omnidirectional, multispectral and multimodal sensor/display processor for the screening, examination, detection, and diagnosis of breast cancer using stable vision fusion of various wavelengths of illumination. Furthermore, U.S. Pat. No. 4,649,275 to Nelson et al., provides a method and apparatus for high-resolution breast imaging which uses collimated light of a narrow spectral bandwidth rather than ionizing X-ray radiation.

Despite expectations, none of the above-cited patents have reached recognized use, if use at all.

However, regardless of the potential advantages, no IR device for soft tissue imaging, including mammography, has been developed to the stage of commercial application and professional acceptance, due to this method's low sensitivity which results from the very high degree of light scatter that characterizes the passage of IR beams through bodily tissue.

It is thus desirable to provide a method and apparatus as a superior alternative to current methods for soft tissue imaging as a procedure that is comfortable for the examinee.

It is another object of the present invention to provide an examination procedure, wherein the exposure to X-rays is totally avoided, resulting in high-quality imaging.

It is a further object of the present invention to provide an apparatus configured to implement the method that is relatively small and inexpensive, so as to fit into, and be suitable for use in a practitioner's office.

DISCLOSURE OF THE INVENTION

Presently, the problems encountered with X-rays mammography relate to unpleasantness and discomfort to the examinee, undesired and unwanted exposure to X-rays, and low quality images making it difficult to detect small size tumors.

A solution to those problems uses beams of light, such as IR light, operative by collection only of those rays directly crossing through the examined tissue along the shortest possible trajectory. To provide a clear image of the illuminated tissue, the direct rays are collected to form a shadowgram image, while deleting stray rays that would blur the image.

The proposed method and apparatus utilizes a source of IR light disposed on a first upstream side of the tissue to be examined, and a unique GaAs image gate and camera, to capture only those rays of light passing straight through the suspect tissue on their exit out of the second opposite downstream side of the examined tissue. The unique GaAs image gate is configured to block-out all undesired stray rays of IR light, allowing the image gate camera to provide a clear shadowgram image.

Thereby, there is provided a shadowgram image that reveals suspect non-uniformity or non-conformity of tissue characteristics, for example, such a featured by cancerous cells.

SUMMARY OF THE INVENTION

It is an object of the present invention to provide a method and an apparatus for detecting non-uniformity or non-conformity in soft tissues, without exposure to X-rays. The method and apparatus for imaging tissue under examination, comprise a source of illumination disposed upstream and emitting light directed onto the tissue for passage therethrough and for exit therefrom as downstream exiting light, an image detector disposed downstream of the tissue for receiving light, and for emitting signals derived from the received light, and a processing unit coupled to the image detector for receiving emitted signals, for processing received signals, and for delivering processed data. The method and apparatus are characterized by the steps of:

coupling the processing unit to and in command of the illumination source for triggering emission of at least one pulse of light lasting for a predetermined duration of time, operating a fast gate coupled to and under command of the processing unit and disposed upstream of the image detector, to open into a first open state and to close into a second closed state in predetermined synchronization with the at least one pulse of light, for selectively permitting passage to the image detector of only ballistic photon rays pertaining to the exiting light, and operating the processing unit to derive an image from the signals received by the image detector. The derived image is displayed on a monitor appropriately coupled to the processing unit.

It is another object of the present invention to provide a method and an apparatus operative with a source of illumination that is configured to emit light selected alone and in combination from the group consisting of invisible light, visible light, coherent light, white light, and infrared light. The source of illumination is configured to emit light in a plurality of different discrete wavelengths of light, and a discrete wavelength, out of the plurality of different discrete wavelengths, is controllably selected, whereby the source of illumination is triggered to emit at least one pulse of light in at least one selected wavelength. Evidently, the source of illumination is configured to emit light in a plurality of different discrete wavelengths of light, and a discrete wavelength out of the plurality of different discrete wavelengths is controllably selected, whereby the source of illumination is triggered to emit a sequence of pulses of light including at least two different wavelengths.

It is a further object of the present invention to provide a method and an apparatus wherein the duration of the at least one pulse of light is selected to last for at least one nanosecond, or to last for less than one nanosecond.

It is yet a further object of the present invention to provide a method and an apparatus wherein the fast gate is operated to open from the closed state into the open state within less than one nanosecond, and even within less than 100 pico-seconds.

It is yet another object of the present invention to provide a method and an apparatus operative wherein the source of illumination is configured to emit light in a plurality of different discrete wavelengths, a discrete wavelength out of the plurality of different discrete wavelengths is controllably selected, and the source of illumination is triggered to emit a sequence of pulses of light including at least two different wavelengths, and a monitor is coupled to the processing unit for displaying an image of superimposed wavelengths derived from the tissue under examination. Since the source of illumination is configured to emit light in a plurality of different discrete wavelengths, the gate is selected to match the wavelength(s) of the emitted light.

It is moreover an object of the present invention to provide a method and an apparatus wherein a time-interval separating two successive pulses out of at least one pulse of light is appropriately controlled by the processing unit to ensure opening of the gate to the open state to allow passage of only ballistic photons.

It is one object of the present invention to provide a method and an apparatus wherein exiting light is directed to pass through a pinhole of small dimension having a first side and a second side, and the gate is supported on either one of both the first side and the second side of the pinhole, and is configured to match the small dimension of the pinhole, whereby a gate of small dimension is operable for tissue imaging.

It is one object of the present invention to provide a method and an apparatus wherein the imaging detector provides enhanced images by incorporating an image amplifier selected from the group consisting of an electron multiplying CCD (Charged Coupled Device), and a CMOS (Complementary Metal-Oxyde Semiconductor) imager with an APD (Avalanche Photodiode Device).

It is one more object of the present invention to provide a method and an apparatus wherein tissue is imaged by upstream illumination and downstream dual filtering of the exiting light for separation of ballistic photons rays from stray rays.

It is yet one more object of the present invention to provide a method and an apparatus wherein the illumination source illuminates the tissue in either one of both single wavelength illumination and multiple wavelength illumination.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 illustrates the trajectory followed by ballistic photons and a shadowgram image of examined tissues, as created by the ballistic photons, FIGS. 2a and 2b shows upstream illumination and downstream light exiting examined tissue along a time axis, FIG. 3 is a schematic illustration of the dual filtering method, FIGS. 4a and 4b are a timing diagram of light exiting examined tissue, and of dually filtered light.

DETAILED DESCRIPTION OF THE PREFERRED EMBODIMENTS

Figure 5:
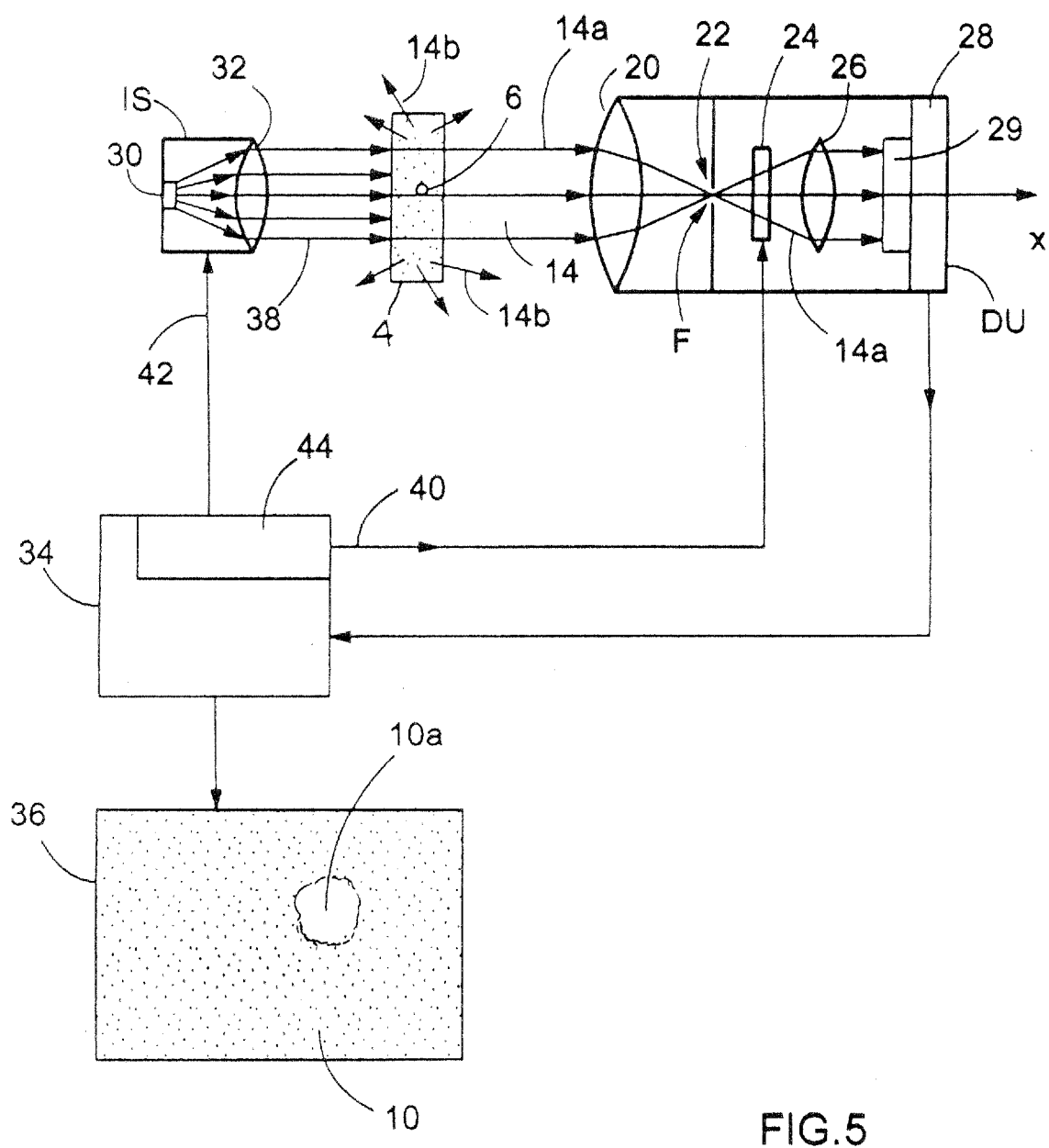
FIG. 5 is a schematic diagram of an apparatus for implementing the IR illumination method for the examination of suspect tissue.

It is known that when a collimated beam of IR illumination passes through examined tissue, most of the light that enters the tissue scatters in all directions. However, a small portion of the entering photons are not scattered. Photons that traverse the tissue in a straight ray, in parallel continuation of the impinging collimated beam, are termed ballistic photons, or BPs.

Ballistic photons, BPs, passing through the examined tissue can be utilized to create a shadowgram image that reveals non-uniformity or non-conformity hidden in the interior of the examined tissue, as is characteristic, for example, with cancer.

FIG. 1 shows a shadowgram image 10, or shadowgram 10, or image 10, created by an upstream originated beam 2 of BPs crossing a tissue 4, which is heterogeneous or non-uniform, in a downstream direction indicated by the arrow A. The number of BPs that exit the tissue 4 at any given point depends on the absorption coefficient of the tissue traversed. That portion of the beam 2 of BPs that manages to pass through a region of high absorption 6, or artifact 6, disposed in the interior of the tissue 4, then exits out of the examined tissue as an attenuated beam 8. The artifact 6 hidden in the interior of tissue 4 therefore appears as shadow 10a that is clearly imaged on the shadowgram 10 created by the beam of BP rays 2.

A shadowgram as described hereinabove is a two-dimensional, 2-D, projection of the examined tissue on a plane perpendicular to the illuminating beam of light. By rotating the imaging device about the examined tissue 4, a series of 2-D projections from different angles are obtained. This series of images is stored, if desired, and processed to provide a 3-D reconstruction of the structure of the examined tissue 4, using known methods and algorithms available and used in conventional x-ray tomography practice.

FIGS. 2a and 2b are two diagrams where the abscissa indicates time and the ordinate are amplitudes. In FIG. 2a, there is shown a flash 12 of light 14 emitted by a source of light illuminating the upstream side of tissue 4 under examination. FIG. 2b depicts the light 14, including BP rays 14a, scattered light rays 14b, exiting the downstream side of the tissue 4, as a function of time. As FIG. 2b clearly shows, BP rays 14a are a small portion of the rays exiting the tissue. The majority of rays are scattered light rays 14b. BP rays 14a exit the examined tissue 4 prior to the time of exit of the scattered rays 14b, since the distance BPs travel through the tissue 4 is shorter.

To obtain a useful image of the examined tissue. BPs 14a must be separated from scattered light 14b, since only a beam of BPs 14a is able to create a clear shadowgram, whereas scattered light 14b, which does not carry the desired information, blurs the picture. The proposed method and apparatus for imaging of tissues utilizes a dual filtering system to separate BP rays 14a from scattered rays 14b, as shown in FIG. 2b.

FIG. 3 depicts a beam of illumination 14 impinging upstream the examined tissue 4, from which the light 14 exits to undergo downstream spatial filtering and temporal filtering. The tissue 4, a collecting lens 20, a pinhole filter 22, a gate 24, a collecting lens 26, and a detector 28 are all shown in the order listed, in alignment, along an optical axis indicated by the arrow X.

The beam of light exiting tissue 4 as a collimated beam of parallel rays, including the BP rays 14a and stray rays 14b, passes first through a focusing lens 20 and converges toward a focus F of that first lens 20. For spatial filtering, a pinhole filter 22 is disposed in the optical path of the converging light rays, at the location of the focal point F, downstream of the focusing lens 20. The pinhole filter 22 permits passage only of parallel BP rays 14a, and prevents scattered rays 14b from passage downstream toward the collecting lens 26 and the image detector 28.

Temporal filtering is achieved by help of a unique GaAs fast gate 24, developed by and proprietary of 3DV Systems Ltd., Yoqneam, Israel, according to the following patents pertaining to fast gating, optical ranging and windowing, all incorporate herewith in whole by reference: U.S. Pat. No. 6,057,909 entitled "Optical ranging camera"; U.S. Pat. No. 6,091,905 entitled "Telecentric 3D camera and method"; U.S. Pat. No. 6,100,517 entitled "Three dimensional camera"; U.S. Pat. No. 6,331,911 entitled "Large aperture optical image shutter"; U.S. Pat. No. 6,483,094 entitled "Solid state optical shutter", and international application No. PCT/IL2005/000942 entitled "Method and apparatus for mapping a retina".

Fast gates, image gates, and fast gating are thus an optical technique developed by and proprietary of 3DV Systems Ltd. of Yokneam, Israel, and are also known in the art as gated intensifiers, or liquid crystal shutters, or opto-electronic shutters, or electro-optical crystal shutters, and as solid-state optical or solid-state opto-electronic very high-speed shutters.

A fast gate, or solid-state optical shutter, is a generally a planar substrate made of semiconductor material, having mutually substantially parallel input and output surfaces controllable by an electrical signal. Fast gates may be switched rapidly between the open and the closed state, with typical very high-speed gate transition times of less than one nanosecond and even as fast as within tens of psec (picoseconds).

When activated, the fast gate 24 is capable of blocking incoming light rays at a sub-nanosecond rise and fall time. It is therefore possible to truncate an incoming light pulse of BP rays 14a immediately after their passage through the gate 24, by shutting the gate 24, to thereby block the passage of the slower scattered light rays 14b, which take a longer time to reach the same fast gate 24 than do BPs, as shown in FIG. 2b. The fast gate 24 is operable for the duration of the at least one pulse of light, which may be selected to last for at least one nanosecond.

It is considered that the duration of at least one pulse of light emitted by the illumination source IS may be selected to last for at least one nanosecond, or for less than one nanosecond. The fast gate 24 is operated accordingly, to open from the closed state into the open state as desired, within less than one nanosecond, and even within less than 100 picoseconds. Evidently, the illumination source IS is not limited to flash a single pulse of light, but may be triggered as desired, to emit a single or a sequence of pulses of light. For a sequence of flashes of light, a time-interval separating two successive pulses of light is appropriately controlled by the processing unit 34 to ensure opening of the gate 24 to the open state to allow passage of only BP rays 14a pertaining to the exiting light 14.

In FIG. 3, showing the dual filtering method, spatial filtering is performed before temporal filtering. Alternative embodiments are possible, wherein temporal filtering is achieved first, and followed later by spatial filtering. Furthermore, the fast gate 24 is possibly disposed at different locations downstream the examined tissue 4 and upstream of the image detector 28. For example, the fast gate 24 may be disposed adjacent to and just upstream or just downstream of the pinhole 22.

FIG. 4a illustrates a sequence of illumination flashes after exit from and downstream of the tissue 4, in sequential alignment along a time axis t, as a succession of light beams 14. Each flash of light 14 features a first faster and smaller beam of BP rays 14a emphasized within dashed lines 30 in FIG. 4a, and a second slower and much larger beam of stray rays 14b.

FIG. 4b depicts the effect of the combined spatial and temporal filtering on the beam of light rays 14 exiting out of the illuminated tissue 4. Since the gate 24 opens for an infinitesimal short amount of time, only the tiny flashes of BP rays 14a pass therethrough. The BP rays 14a are distributed in successively spaced apart alignment along the time axis t, on their way downstream toward the detector 28. As described hereinabove, after spatial and temporal filtering, the scattered light rays 14b are excluded from passage downstream and are prevented from reaching the image detector 28.

FIG. 5 is a schematic diagram of an integrated gated TR imaging apparatus, which is a preferred embodiment 200 applying the described method. The examined tissue 4 is disposed between an illumination source IS and a detection unit DU. Both the illumination source IS and the detection unit DU are kept in optical alignment along an axis x, by means not shown in FIG. 5, for the sake of simplicity.

The illumination source IS, having a source 30 of light 14, such as IR light, and a collimating lens 32, emits pulsed light as collimated IR illumination beams 38. A processor 34, or processing unit 34, is coupled to the illumination source IS, and incorporates a triggering unit 44, which sends illumination triggering signals 42. When a triggering signal 42 is received by the illumination source IS, the IR source 30 of IR light emits a pulse of IR light, which is collimated by the collimating lens 32.

The collimated IR beams 38 pass from upstream, through the examined tissue 4 and then downstream, but the largest portion of the IR beams 38 scatter in the interior of the tissue 4 as stray rays 14b, while only a small portion of the IR beam 38 pass straight through and exit the tissue 4 in the form of BP rays 14a. The light beams exiting from the tissue 4 continue downstream towards the detection unit DU, wherein temporal filtering and detection takes place.

Light beams 14a entering the detection unit DU, are first focused by an objective lens 20, to converge toward the focal point F of the lens 20. A pinhole filter 22, disposed downstream of lens 20 at the focal point F, acts as a spatial filter, filtering out the scattered rays 14b, and permitting passage only of BP rays 14a.

In turn, the IR light reaches a fast gate 24, disposed downstream of the pinhole filter 22, to collect the BP rays 14a and operate as a temporal filter.

The triggering unit 44 synchronizes the gate 24 with the source 30 of IR light. For each illumination-triggering signal 42 emitted by the triggering unit 44 to the source 30 of IR light, the triggering unit 44 also emits a corresponding synchronized gating signal 40 to the gate 24. The two triggering signals, 40 and 42, are synchronized so that for each pulse of IR light emitted by the source 30, the gate 24 opens just long enough to selectively permit passage of the BP rays 14a to the image detector 28, and then closes in time before the arrival of any residual scattered light rays 14b. The gate 24 is thus configured to open into a first open state and to close into a second closed state in predetermined synchronization with the at least one pulse of light 14, under command of the processor 34.

Light beams exiting the gate 24 are collected downstream and collimated again into a collimated beam of light, by a collecting lens 26. The re-collimated beam of light creates an image on an image detector 28, possibly a CCD or CMOS detector, sensitive to the specific IR wavelength used. If desired, the image detector 28 incorporates an image amplifier 29.

The image amplifier 29 is selected form devices known in the art, for example from the group consisting of an electron multiplying CCD (Charged Coupled Device), and a CMOS (Complementary Metal-Oxyde Semiconductor) imager with an APD (Avalanche Photodiode Device).

The image detector 28 forwards detected images to the processor 34 to which it is coupled, and which has a memory, not shown in FIG. 5, in which images and application programs may be stored. The processor 34 is configured to derive an image from the signals received from the image detector 28, to run image-processing programs, and to deliver processed data that can be used to enhance the detected image. As desired, raw images or processed images are displayed on a monitor 36, or display 36, which is coupled to processor 34. The resulting image is a shadowgram 10, obtained from the tissue 4, showing a shadow 10a of a high absorption lump 6 within the tissue 4.

As described in the international application No. PCT/IL2005/000942, the illumination source IS is, if desired, a source 30 of IR light that may illuminate by emitting one single wavelength $\lambda$, or emit a range of wavelengths $\lambda i$, with i=i [1, 2, 3, . . . , n], flashing one single wavelength $\lambda i$ at a time, or in a combination of wavelengths, either successively or simultaneously, as selected. The illumination source IS is not limited to any particular number n of wavelengths, but is configured as desired. Thus, the source of illumination IS is configured to flash for a predetermined duration of time, a single wavelength, a plurality of wavelengths, or a combination of wavelengths, always with appropriately wavelength-matched gates 24, and image detectors 28.

The source of illumination IS is configured to emit, as desired, visible light, invisible light, coherent light, white light, and infrared light. Likewise the source of illumination IS may emit light in a single wavelength $\lambda$, or a plurality of different discrete selectable wavelengths of light $\lambda i$, with i=1, 2, 3, . . . n.

Evidently, the image detector 28 is appropriately configured to capture the emitted wavelength(s) $\lambda i$ or $\lambda n$. Since the derived images 10, or shadowgrams 10, are processed by the processor 34 implementing a processing method written in the form of a computer program stored in the program memory of the processor, not shown in the Figs., it is possible when the embodiment 200 is rotated about the tissue 4, to display 3-D images on the monitor 36. Furthermore, images 10 derived under various wavelengths $\lambda i$ are easily superimposed for display on the monitor 36, or on more than one monitor.

INDUSTRIAL APPLICABILITY

Industrial applicability is self-evident and similar to that of other diagnostic tools used by medical-care imaging specialists.

It will be appreciated by persons skilled in the art, that the present invention is not limited to what has been particularly shown and described hereinabove. Rather, the scope of the present invention is defined by the appended claims and by the patents incorporated herewith in whole, and includes both combinations and subcombinations of the various features described hereinabove as well as variations and modifications thereof which would occur to persons skilled in the art upon reading the foregoing description. For example, by applying the techniques disclosed in the application No. PCT/IL2005/000942, images are derived in more than one wavelength.

The invention claimed is:

1. A method for imaging tissue under examination, comprising:
   a source of illumination disposed upstream and emitting light directed onto the tissue for passage therethrough and for exit therefrom as downstream exiting light,
   an image detector disposed downstream of the tissue for receiving light, and for emitting signals derived from the received light,
   a processing unit coupled to the image detector for receiving emitted signals, for processing received signals, and for delivering processed data, the method being comprising the steps of:
   coupling the processing unit to and in command of the illumination source for triggering emission of at least one pulse of light lasting for a predetermined duration of time,
   operating a fast gate coupled to and under command of the processing unit and disposed upstream of the image detector, to open into a first open state and to close into a second closed state in predetermined synchronization with the at least one pulse of light for selectively permitting passage to the image detector of only ballistic photon rays pertaining to the exiting light, and
   operating the processing unit to derive an image from the signals received by the image detector.

2. The method according to claim 1, wherein:
   the derived image is displayed on a monitor appropriately coupled to the processing unit.

3. The method according to claim 1, wherein:
   the source of illumination is configured to emit light selected alone and in combination from the group consisting of invisible light, visible light, coherent light, white light, and infrared light.

4. The method according to claim 1, wherein:
   the source of illumination is configured to emit light in a plurality of different discrete wavelengths of light, and
   a discrete wavelength out of the plurality of different discrete wavelengths, is controllably selected,
   whereby the source of illumination is triggered to emit at least one pulse of light in at least one selected wavelength.

5. The method according to claim 1, wherein:
   the source of illumination is configured to emit light in a plurality of different discrete wavelengths of light, and a discrete wavelength out of the plurality of different discrete wavelengths is controllably selected, whereby the source of illumination is triggered to emit a sequence of pulses of light including at least two different wavelengths.

6. The method according to claim 1, wherein:
the duration of the at least one pulse of light is selected to last for at least one nanosecond.

7. The method according to claim 1, wherein:
the duration of the at least one pulse of light is selected to last for less than one nanosecond.

8. The method according to claim 1, wherein:
the fast gate is operated to open from the closed state into the open state within less than one nanosecond.

9. The method according to claim 1, wherein:
the fast gate is operated to open from the closed state into the open state within less than 100 picoseconds.

10. The method according to claim 1, wherein:
the source of illumination is configured to emit light in a plurality of different discrete wavelengths,
a discrete wavelength out of the plurality of different discrete wavelengths is controllably selected, and the source of illumination is triggered to emit a sequence of pulses of light including at least two different wavelengths, and
a monitor is coupled to the processing unit for displaying an image of superimposed wavelengths derived from the tissue under examination.

11. The method according to claim 1, wherein:
the source of illumination is configured to emit light in a plurality of different discrete wavelengths,
the gate is selected to match the wavelength(s) of the emitted light.

12. The method according to claim 1, wherein:
a time-interval separating two successive at least one pulse of light is appropriately controlled by the processing unit to ensure opening of the gate to the open state to allow passage of only ballistic photons.

13. The method according to claim 1, wherein:
exiting light is directed to pass through a pinhole of small dimension having a first side and a second side, and
the gate is supported on either one of both the first side and the second side of the pinhole and is configured to match the small dimension of the pinhole,
whereby a gate of small dimension is operable for tissue imaging.

14. The method according to claim 1, wherein:
the imaging detector provides enhanced images by incorporating an image amplifier elected from the group consisting of an electron multiplying CCD (Charged Coupled Device), and a CMOS (Complementary Metal-Oxyde Semiconductor) imager with an APD (Avalanche Photodiode Device).

15. The method according to claim 1, wherein:
tissue is imaged by upstream illumination and downstream dual filtering of the exiting light for separation of ballistic photons rays from stray rays.

16. The method according to claim 1, wherein:
the illumination source illuminates the tissue in either one of both single wavelength illumination and multiple wavelength illumination.

17. An apparatus for imaging tissue under examination, comprising:
a source of illumination disposed upstream and emitting light directed onto the tissue for passage therethrough and for exit therefrom as downstream exiting light, an image detector disposed downstream of the tissue for receiving light, and for emitting signals derived from the received light,
a processing unit coupled to the image detector for receiving emitted signals, for processing received signals, and for delivering processed data, the apparatus comprising:
the processing unit being coupled to and in command of the illumination source for triggering emission of at least one pulse of light lasting for a predetermined duration of time,
a fast gate coupled to and under command of the processing unit and disposed upstream of the image detector, to open into a first open state and to close into a second closed state in predetermined synchronization with the at least one pulse of light, for selectively permitting passage to the image detector of only ballistic photon rays pertaining to the exiting light, and
the processing unit being operated to derive an image from the signals received by the image detector.

18. The apparatus according to claim 17, wherein:
the derived image is displayed on a monitor appropriately coupled to the processing unit.

19. The apparatus according to claim 17, wherein:
the source of illumination is configured to emit light selected alone and in combination from the group consisting of invisible light, visible light, coherent light, white light, and infrared light.

20. The apparatus according to claim 17, wherein:
the source of illumination is configured to emit light in a plurality of different discrete wavelengths of light, and
a discrete wavelength out of the plurality of different discrete wavelengths, is controllably selected,
whereby the source of illumination is triggered to emit at least one pulse of light in at least one selected wavelength.

21. The apparatus according to claim 17, wherein:
the source of illumination is configured to emit light in a plurality of different discrete wavelengths of light, and
a discrete wavelength out of the plurality of different discrete wavelengths is controllably selected,
whereby the source of illumination is triggered to emit a sequence of pulses of light including at least two different wavelengths.

22. The apparatus according to claim 17, wherein:
the duration of the at least one pulse of light is selected to last for at least one nanosecond.

23. The apparatus according to claim 17, wherein:
the duration of the at least one pulse of light is selected to last for at least one nanosecond.

24. The apparatus according to claim 17, wherein:
the duration of the at least one pulse of light is selected to last for less than one nanosecond.

25. The apparatus according to claim 17, wherein:
the fast gate is operated to open from the closed state into the open state within less than 100 picoseconds.

26. The apparatus according to claim 17, wherein:
the source of illumination is configured to emit light) in a plurality of different discrete wavelengths,
a discrete wavelength out of the plurality of different discrete wavelengths is controllably selected, and the source of illumination is triggered to emit a sequence of pulses of light including at least two different wavelengths, and
a monitor is coupled to the processing unit for displaying an image of superimposed wavelengths derived from the tissue under examination.

27. The apparatus according to claim 17, wherein:
the source of illumination is configured to emit light in a plurality of different discrete wavelengths,
the gate is selected to match the wavelength(s) of the emitted light.

28. The apparatus according to claim 17, wherein:
a time-interval separating two successive at least one pulse of light is appropriately controlled by the processing unit to ensure opening of the gate to the open state to allow passage of only ballistic photons.

29. The apparatus according to claim 17, wherein:
exiting light is directed to pass through a pinhole of small dimension having a first side and a second side, and
the gate is supported on either one of both the first side and the second side of the pinhole, and is configured to match the small dimension of the pinhole,
whereby a gate of small dimension is operable for tissue imaging.

30. The apparatus according to claim 17, wherein:
the imaging detector provides enhanced images by incorporating an image amplifier selected from the group consisting of an electron multiplying CCD (Charged Coupled Device), and a CMOS (Complementary Metal-Oxyde Semiconductor) imager with an APD (Avalanche Photodiode Device).

31. The apparatus according to claim 17, wherein:
tissue is imaged by upstream illumination and downstream dual filtering of the exiting light for separation of ballistic photons rays from stray rays.

32. The method according to claim 17, wherein:
the illumination source illuminates the tissue in either one of both single wavelength illumination and multiple wavelength illumination.

\* \* \* \* \*